US008743918B2

United States Patent
Givon et al.

(10) Patent No.: US 8,743,918 B2
(45) Date of Patent: Jun. 3, 2014

(54) PHASE LOCKED SIDEBAND BEAMS BY BIAS MODULATION OF AN EXTERNAL CAVITY LASER DIODE HAVING A GRATING

(75) Inventors: Menachem Givon, D.N. Hanegev (IL); Amir Waxman, Jaffa (IL)

(73) Assignee: Ben Gurion University of the Negev, Research and Development Authority, Beer Sheva (IL)

( * ) Notice: Subject to any disclaimer, the term of this patent is extended or adjusted under 35 U.S.C. 154(b) by 397 days.

(21) Appl. No.: 13/120,656

(22) PCT Filed: Sep. 24, 2009

(86) PCT No.: PCT/IB2009/054179
§ 371 (c)(1),
(2), (4) Date: Mar. 24, 2011

(87) PCT Pub. No.: WO2010/041158
PCT Pub. Date: Apr. 15, 2010

(65) Prior Publication Data
US 2011/0168913 A1 Jul. 14, 2011

Related U.S. Application Data

(60) Provisional application No. 61/136,870, filed on Oct. 10, 2008.

(51) Int. Cl.
*H01S 3/10* (2006.01)
*H01S 3/13* (2006.01)
(52) U.S. Cl.
USPC .................................. 372/28; 372/26; 372/32

(58) Field of Classification Search
USPC .......... 372/26, 28, 29.022, 32, 38.1, 102, 108
See application file for complete search history.

(56) References Cited

U.S. PATENT DOCUMENTS

| | | | | |
|---|---|---|---|---|
| 6,804,278 B2* | 10/2004 | Daiber et al. | | 372/38.01 |
| 6,816,516 B2* | 11/2004 | Daiber | | 372/20 |
| 7,733,924 B2* | 6/2010 | Wysocki et al. | | 372/20 |
| 2003/0016709 A1* | 1/2003 | Flanders | | 372/26 |

OTHER PUBLICATIONS

Waxman A et al :"Modulation enhancement of a laser diode in an external cavity" Applied Physics B; Lasers and Optics, Spribger, Berlin, DE, vol. 95, No. 2. Jan. 14, 2009, pp. 301-305.

* cited by examiner

*Primary Examiner* — Armando Rodriguez
(74) *Attorney, Agent, or Firm* — Mark M. Friedman (57) ABSTRACT

A device and a method enabling the enhancing of the modulation efficiency of lasers by matching the modulation frequency and the FSR of the laser. This is optionally achieved by eliminating the internal cavity of a laser diode (103) placed in an external cavity and matching the FSR of the external cavity to the modulation frequency. The modulation index is enhanced to and beyond the point of complete carrier suppression even at high modulation frequency and high beam intensities. The external cavity comprises a grating (107), the cavity length being adjusted with a PZT (108) and a translation stage (109). The laser diode (103) is driven by a bias current (110) from a driver (115) and a modulation current (111) from a modulation driver (116).

4 Claims, 8 Drawing Sheets

PHASE LOCKED SIDEBAND BEAMS BY BIAS MODULATION OF AN EXTERNAL CAVITY LASER DIODE HAVING A GRATING

REFERENCE TO CROSS-RELATED APPLICATION

This application claims priority from U.S. Provisional Application No. 61/136,870, filed on Oct. 10, 2008, herein incorporated by reference in its entirety.

FIELD OF THE INVENTION

The present invention relates to lasers, and more particularly, to enhancement of the modulation efficiency of lasers by matching the modulation frequency and the FSR of the lasers.

BACKGROUND OF THE INVENTION

High frequency modulation of laser beams is an important tool in many fields, such as communication, atomic physics and many others. In particular, the experimental realization of a Λ-system sets the ground for many applications of precision measurements.

Some of these applications include atomic clocks [1, 2], magnetic sensors [3] and gravity gradiometers [4]. This Λ-system consists of two coherent laser fields, two hyperfine levels of an atomic ground state and an excited state. Depending on the application, the coherent coupling of the two sub levels of the ground state is done by laser beams which are resonant (as in CPT) or non resonant (as in Stimulated Raman transitions) with the transition to the excited state. In both cases the beams must be phase locked and with a tunable frequency difference in the range of several GHz (corresponding to the ground state's hyperfine split energy in alkali atoms).

Three main methods have been developed over the years for the generation of the two phase-locked beams: Direct light modulation either by AOM [5] or EOM [6, 7], optical phase locking of two lasers [8, 9] and direct current modulation of a laser diode [10]. The modulation of the DC current injected to the laser diode by an AC signal of the frequency $f_m$ produces optical side bands. The first order sidebands can then be injected to slave lasers for amplification and spectral purification. The final result is two phase locked laser beams with a frequency difference of $2f_m$. However, the modulation response of edge emitting diode laser decreases sharply as the modulation frequency increases.

An alternative is to modulate the current of a vertical cavity surface-emitting laser (VCSEL) [11] which is much more susceptible to high frequency modulation but has very little power (total of 2 mw).

In the present patent application experimental results are presented, demonstrating the modulation response enhancement of an AR coated edge emitting laser diode in an external cavity.

By eliminating the internal cavity of the laser diode and matching the modulation frequency to the FSR of the external cavity per the present invention the modulation index is enhanced to the point of complete carrier suppression even at high modulation frequency. The result is a tunable modulation source in the range of 3 to 6 GHz, with more then 60% of the total power of the output beam concentrated in the two first optical sidebands.

Modulation enhancement by an external resonance cavity with a mode spacing corresponding to the desired modulation frequency was already reported both for edge emitting diodes [12] and VCSEL [13]. However, as the internal resonance cavity of these diodes was not eliminated, complete carrier suppression was not demonstrated in these experiments, or complete carrier suppression was demonstrated, only when the power of the beam was small.

The modulation enhancement of a "regular" (FP) diode (like the one used in [12]) is compared to that of the AR coated diode, to illustrate the effect of the elimination of the internal resonance cavity. The affect of the DC current on the modulation response is also examined.

Figure 1:
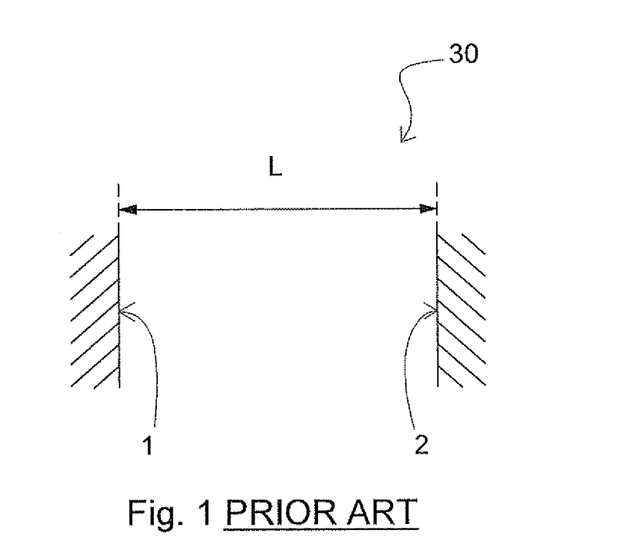
FIG. 1 of the prior art is a schematic illustration of a resonance cavity of distance L, having a first reflective surface, and a second reflective surface, which are parallel and facing each other.

FIG. 1 of the prior art is a schematic illustration of a resonance cavity 30 of distance L, having back reflector 1 which is a high reflectivity mirror, and an output coupler 2 which is a mirror with partial transmission.

As used herein the specification and in the claims section that follows, the term "FSR", (free spectral range), and the like refer to the basic resonance frequency of a resonance cavity.

FSR is given by:

$$FSR = \frac{c}{2L_{eff}}, L_{eff} = L_1 n_1 + L_2 n_2 + (L - L_1 - L_2)n \quad (1)$$

were c is the speed of light and $L_{eff}$ is the effective length of the resonance cavity.

$L_{eff}=L$, if the space inside the resonance cavity is empty.

$L_{eff}=n \times L$, if the space inside the resonance cavity is filled with a material with refractive index n.

$L_{eff}=n_1 \times L_1 + n_2 \times L_2 + \ldots$ if there are several materials inside the resonance cavity.

Figure 2:
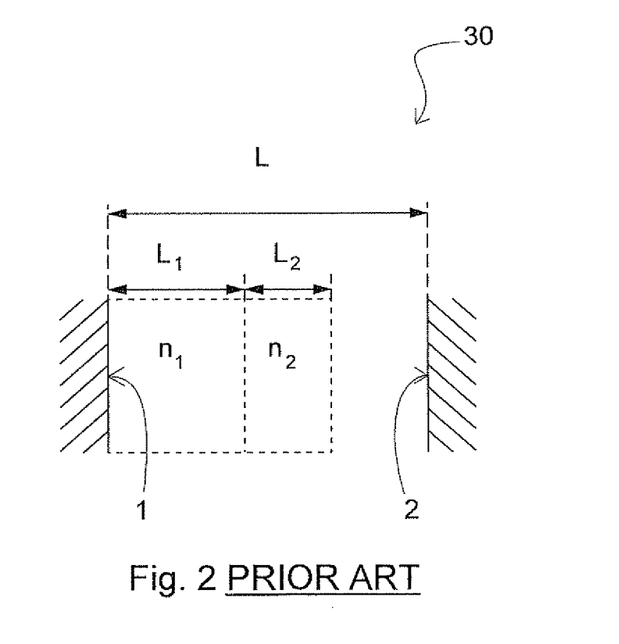
FIG. 2 of the prior art is a schematic illustration of a resonance cavity with several materials, having several indices n along its length L.

FIG. 2 of the prior art is a schematic illustration of a resonance cavity 30 with several materials, having several indexes n along its length L. The first material is spread along $L_1$ and has indexes $n=n_1$, the second material is spread along $L_2$ and has indexes $n=n_2$, etc.

Lasing Frequency

The laser will emit light at a frequency v that is an integer multiplication of the FSR (resonance condition):

$$v = k \times FSR, k=1,2,3,\ldots \quad (2)$$

Typically, the value of k for an operating laser is between $10^5$ and $10^7$.

Direct Laser Modulation

In some lasers it is possible to introduce periodic perturbation to the amplification means (gain medium) of the laser. As a result, the laser light's spectrum will include additional components, known as sidebands. In this case the laser field is given by:

$$E = E_0 e^{i\omega t} + E_{k\pm} e^{i(\omega \pm k\omega_m)t}, k=1,2,3 \ldots \quad (3)$$

Where $\omega=2\pi v$ is the main laser angular frequency (also known as the carrier frequency), and $\omega_m=2\pi f_m$ is the modulation angular frequency. $E_0$ is the amplitude of the carrier and $E_{k\pm}$ are the amplitudes of the sidebands.

Modulation Index (Depth)

The amplitudes of the carrier and the sidebands are approximately propositional to the Bessel functions of the first kind:

$$E_0 \propto J_0(m), E_{k\pm} \propto \pm J_k(m) \quad (4)$$

The dimensionless parameter m is an indicator to the modulation strength. For m<0.1 there will be no noticeable modulation. At m=0.4, the first order sidebands (k=1) will have about 4% of the energy each, and the second sideband will emerge. At m=2.4, the carrier amplitude goes to zero ("full carrier suppression") and all the energy is split between the first 4 sidebands. As m increases, more sidebands will appear in the laser beam.

Typically, direct modulation of a laser beam is achieved by modulating the DC current supply of a laser diode with an AC current source. Changing the AC frequency directly controls the modulation angular frequency $\omega_m$. The modulation index m is dependent on several factors: The ratio between the DC and AC power, the dissipation of AC along the diode feeding circuit, reflection of part of the AC power due to imperfect impedance matching and the susceptibility of the diode's material to the AC modulation. On top of all these parameters, as the modulation frequency goes up to the GHz range, the optical sidebands move noticeably away from the resonance condition (2), and are thus strongly suppressed by the laser resonance cavity itself, as shown in FIG. 3.

Figure 3:
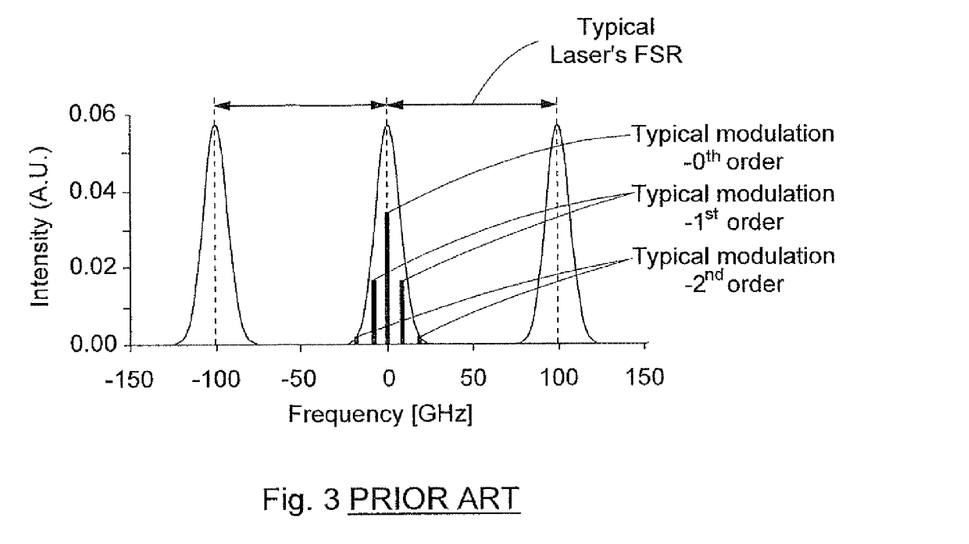
FIG. 3 of the prior art is a graphical illustration of the suppression of the amplitude of the modulated sidebands due to the effect of the resonance condition.

FIG. 3 of the prior art is a graphical illustration of the suppression of the amplitude of the modulated sidebands due to the effect of the resonance condition There is a need for a method and a device for enhancing the modulation efficiency of lasers.

SUMMARY OF THE INVENTION

The present invention of an FSR-matched modulated laser is a device and a method that enables modulation of high power laser beams at high frequency and with high modulation index. This method enhances the modulation response of the laser, as measured either by the modulation index or by the percentage of the power that is transferred from the un-modulated laser beam to the modulated sidebands. The modulation enhancement is optionally achieved by matching the FSR (1) of the laser's resonance cavity to the modulation frequency $f_m$, or optionally by matching the FSR (1) of the laser's resonance cavity to $f_m/n$, n=2, 3, 4 . . . . In both cases, all the sidebands fulfill the resonance condition (2) and are thus amplified by the laser's resonance cavity and gain material. Optionally, modulation enhancement can be achieved by matching the FSR (1) of the laser's resonance cavity or to $2 \times f_m$. In this case, only the un-modulated beam and the even sidebands fulfill the resonance condition (2) and are thus amplified by the laser's resonance cavity and gain material. In this case the odd sidebands do not fulfill the resonance condition (2) and are thus strongly suppressed by the laser's resonance cavity.

Modulated laser beams find diversified usage: in optical communication, atomic clocks, magnetometers, radar systems, manipulation of quantum states in modern quantum mechanics research and many other applications. Providing a device and a method for enhanced modulation of laser beams might have a significant impact, either by providing cheaper modulated lasers or by providing additional applications of modulated laser beams Additional objects and advantages of the invention will be set forth in part in the description which follows and, in part, will be obvious from the description, or may be learned by practice of the invention.

According to the present invention there is provided an FSR-matched modulated laser with enhanced modulation efficiency, the FSR-matched modulated laser including: (a) a M-laser, the M-laser including: (i) a back reflector; (ii) an output coupler, having a mirror with partial transmission quality, wherein the output coupler is positioned facing the back reflector with a distance L between the output coupler and the back reflector, wherein the distance L is a cavity length; (iii) a gain medium disposed between the output coupler and the back reflector; and (iv) a light modulation means disposed between the output coupler and the back reflector, wherein the M-laser has a free spectral range, wherein the modulation means has a modulation means frequency $f_m$, and wherein the modulation means frequency $f_m$ is equal to an integer times the free spectral range.

According to further features in described embodiments of the invention described, the modulation means $f_m$ is equal to one half of the free spectral range.

According to further features in described embodiments of the invention described, the FSR-matched modulated laser further including: (b) a modulation source including: (i) a laser power supply; (ii) a bias T; (iii) a power line, the power line feeding power from the laser power supply to the bias T; (iv) a modulation generator; (v) a bias T modulation line, the bias T modulation line feeding modulation signal from the modulation generator to the bias T; (vi) a laser feed line, the laser feed line feeding the power from the bias T to the gain medium; and (vii) a direct modulation line, the direct modulation line feeding the modulation signal from the modulation generator to the light modulation means.

According to further features in described embodiments of the invention described, the cavity length is adjustable.

According to further features in described embodiments of the invention described, the cavity length is adjustable, by moving of the output coupler.

According to further features in described embodiments of the invention described, the cavity length is adjustable, by moving the back reflector.

According to further features in described embodiments of the invention described, the refractive index of the gain medium is adjustable.

According to another embodiment of the invention an FSR-matched modulated AR laser with enhance modulation efficiency, the FSR-matched modulated AR laser including: (a) an external cavity diode laser including: (i) an AR diode, having a front facet, a back facet, a diode gain material, and a lens, wherein the front facet is coated with anti reflection films; (ii)

a grating, positioned such that part of an internal AR laser beam that hits the grating is reflected back and another part of the internal AR laser beam is reflected to an output direction as an output AR laser beam; (iii) a piezoelectric transducer, wherein the piezoelectric transducer is firmly connected to the grating; and (iv) a mechanical translation stage, wherein the piezoelectric transducer is firmly connected to the translation stage, wherein the piezoelectric transducer can move in a motion direction which is aligned parallel to a direction of the internal AR laser beam, wherein the FSR-matched modulated AR laser has a free spectral range, wherein the FSR-matched modulated AR laser is modulated by a modulation means having a modulation means frequency $f_m$, and wherein the modulation means frequency $f_m$ is equal to an integer times the free spectral range.

According to further features in described embodiments of the invention described, the modulation means $f_m$ is equal to one half of the free spectral range.

According to further features in described embodiments of the invention described, by applying electric voltage to the piezoelectric transducer a position of the grating relative to the translation stage can be fine tuned.

According to further features in described embodiments of the invention described, the FSR-matched modulated AR laser further including: (b) an AR modulation source including: (i) an AR modulation source, for supplying power to the gain medium; (ii) an AR modulation generator, that produces a modulation signal, which is a periodic electrical signal at frequency $f_m$; (iii) an AR Bias T, for superimposing the power with the modulation signal; (iv) an AR power line, the AR power line feeding the power from the AR laser power supply to the AR Bias; (v) an AR bias T modulation line, the AR bias T modulation line feeding the modulation signal from the AR modulation generator to the bias T; and (vi) an AR laser feed line, the AR laser feed line feeding the power superimposed with the modulation signal from the bias T to the gain medium, wherein the supplying of the power to the gain medium is done through the AR bias T.

BRIEF DESCRIPTION OF THE DRAWINGS

The invention is herein described, by way of example only, with reference to the accompanying drawings, wherein.

DETAILED DESCRIPTION OF EMBODIMENTS

The present invention is of a system and a method for enhancement of the modulation efficiency of laser by matching the modulation frequency and the FSR of the laser.

The principles and operation of a system and a method according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings.

Unless otherwise defined, all technical and scientific terms used herein have the same meaning as commonly understood by one of ordinary skill in the art to which this invention belongs. The materials, dimensions, methods, and examples provided herein are illustrative only and are not intended to be limiting.

LIST OF REFERENCES

[1] V. Shah, S. Knappe, L. Hollberg, and J. Kitching, Opt. Lett. 32, 12441246 (2007).

[2] H. S. Moon, S. E. Park, Y. Park, L. Lee, and J. B. Kim, J. Opt. Soc. Am. B 23, 23932397 (2006).

[3] P. Schwindt, S. Knappe, V. Shah, L. Hollberg, J. Kitching, L. Liew and J. Moreland, Appl. Phys. Lett. 85, 6409 (2004)

[4] N. Yu, J. M. Kohel, L. Romans and L. Maleki, Quantum gravity gradiometer sensor for earth science applications, ESTC 2002, Pasadena, Calif. (2002).

[5] P. Bouyer, T. L. Gustavson, K. G. Haritos, M. A. Kasevich, Opt. Lett. 18, 649 (1993).

[6] M. Kasevitch, S. Chu, Phys. Rev. Lett. 69, 1741 (1992).

[7] K. Szymaniec, S. Ghezali, L. Coghnet, A. Clairon, Opt. Commun. 144, 51 (1997).

[8] G. Santarelli, A. Clairon, S. N. Lea, G. Tino, Opt. Commun. 104, 339 (1994).

[9] M. J. Snadden, R. B. M. Clarke, E. Riis, Opt. Lett. 22, 892 (1997).

[10] J. Ringot, Y. Lecoq, J. C. Garreau and P. Szriftgiser, Eur. Phys. J. D, 65, 285, (1999).

[11] C. A®olderbach, A. Nagel, S. Knappe, C. Jung, D. Wiedenmann, and R. Wynands, Appl. Phys. B: Lasers Opt. 70, 407 (2000).

[12] C. J. Myatt, N. R. Newbury, and C. E. Wieman, Opt. Lett. 18, 649 (1993).

[13] N. Gavra, V. Ruseva, and M. Rosenbluh, App. Phys. Lett. 92, 221113 (2008).

[14] S. Kobayashi, Y. Yamamoto, M. Ito, and T. Kimura, IEEE Journal of Quantum Electronics, QE-18, 4, 582 (1982).

As used herein in the specification and in the claims section that follows, the term "laser" (light amplification by stimulated emission of radiation) and the like refer to a resonance cavity for electromagnetic (EM) radiation and means (located inside the resonance cavity) for the amplification of the electromagnetic radiation while the radiation is inside the resonance cavity. The laser is a source of intense light in the ultraviolet, visible or infrared region of the spectrum.

As used herein in the specification and in the claims section that follows, the term "resonance cavity", and the like refer to a pair of parallel reflective surfaces, at a distance L from each other, where the reflective side of each reflective surface faces the other reflective surface.

As used herein in the specification and in the claims section that follows, the terms "Anti-reflective coating", "AR coating", "AR", and the like refer to applying coating to a surface so that this surface will not reflect light.

As used herein in the specification and in the claims section that follows, the terms "AR diode" and the like refer to a laser diode in which the output coupler of the diode is AR coated.

Figure 4:
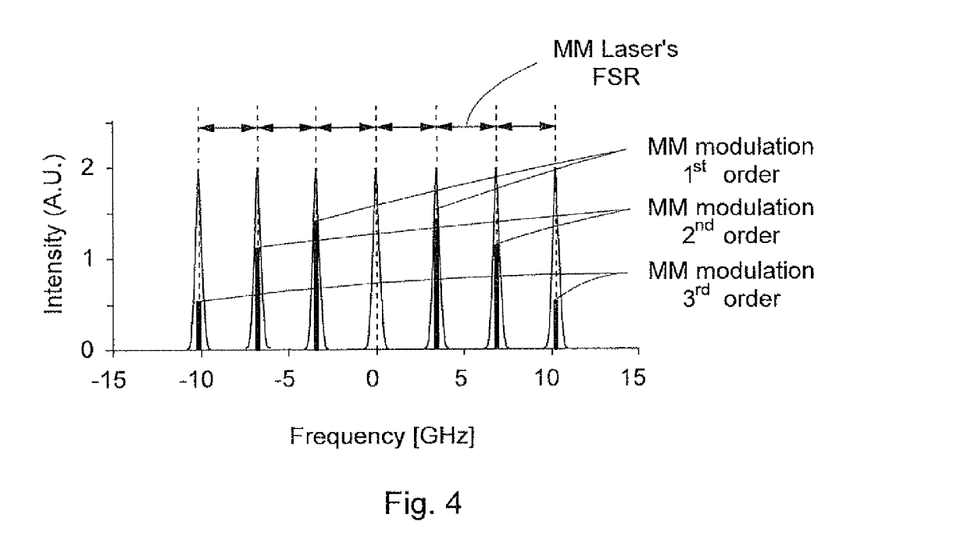
FIG. 4 is a graphical illustration of enhancement of the amplitude of the modulated sidebands due to the matching of the FSR of the laser's resonase cavity to the modulation frequency, in accordance with an embodiment of the present invention.

The following list is a legend of the numbering and description of the application illustrations:

1 back reflector, a high reflectivity mirror
2 output coupler, a mirror with partial transmission
3 gain medium, a medium that amplifies the intensity of light passing through it
4 light modulation means, device or medium that can modulate internal laser beam 20 or output laser beam 21 with a modulation signal at frequency $f_m$
5 laser power supply, means for supplying power, optionally, through bias T 7, to gain medium 3
6 modulation generator, means that produces the modulation signal—a periodic electrical signal at frequency $f_m$
7 bias T, means for superimposing the power with the modulation signal
10 power line, line that feed the power from laser power supply 5 to bias T 7
11 bias T modulation line, line that feed the modulation signal from modulation generator 6 to the bias T 7
12 laser feed, line, line that feeds the power (optionally superimposed with the modulation signal) from bias T 7 to gain medium 3
13 direct modulation line, line that feed the modulation signal from modulation generator 6 to light modulation means 4
20 internal laser beam, laser beam between the back reflector 1 and the output coupler 2
21 output laser beam, laser beam that is transmitted by the output coupler 2 out of the FSR-matched modulated laser
30 resonance cavity
50 M-laser, the subsystem comprised of back reflector 1, the output coupler 2, gain medium 3, internal laser beam 20, output laser beam 21 and optionally light modulation means 4
51 modulation source, the subsystem comprised of the laser power supply 5, modulation generator means 6, bias T 7, power line 10, bias T modulation line 11, laser feed line 12 and direct modulation line 13
101 back facet, back facet of the AR diode 150
102 front facet, AR coated front facet of the AR diode 150
103 diode gain material, gain material of the AR diode 150
104 lens, used for collimation of AR internal laser beam 120 as it comes out of the front facet 102
107 grating, positioned such that part of the internal AR laser beam 120 that comes from the front facet 102 of the AR diode 150 and hits the grating is reflected back towards the front facet 102 of the AR diode 150 and another part of the internal AR laser beam 120 is refracted into the direction of the output AR laser beam 121
108 PZT, a piezoelectric transducer (PZT) that is on one side firmly connected to the translation stage 109 and on the other side firmly connected to grating 107. By applying electric voltage of typically 0 to 500V or typically 0 to 1000V to the PZT the position of the grating 107 relative to the translation stage 109 can be fine tuned, typically by less than 0.1 micrometer/volt
109 translation stage, a mechanical means for controlling the cavity length L. In one embodiment the translation stage is a mechanical means that can move the PZT 108 and the grating 107 firmly connected to one side of the PZT 108. The direction of motion of the translation stage 109 is aligned parallel to the internal AR laser beam 120. The movement is typically in the range of 25 mm or of 50 mm
110 AR power line, line that feeds the power from the AR power supply 115 to the AR Bias T 117
111 AR Bias T modulation line, line that feeds the modulation signal from AR modulation generator 116 to the bias T 117
112 AR laser feed line, line that feeds the power superimposed with the modulation signal from the bias T 117 to the diode gain material 103.
115 AR power supply, means for supplying power through the AR bias T 117 to diode gain material 103
116 AR modulation generator, means that produces the modulation signal—a periodic electrical signal at frequency $f_m$
117 AR bias T, means for superimposing the power with the modulation signal
120 internal AR laser beam, laser beam between the back facet 101 and the grating 107
121 output AR laser beam, laser beam that is reflected by the grating 107 out of the FSR-matched modulated AR Laser 2000
130 external cavity laser diode (ECLD)
141 Fabry Perot (FP) interferometer
142 oscilloscope
143 computer
150 AR diode, edge emitting laser diode where the front facet is coated with anti reflection (AR) films. The AR diode is comprised of back facet 101, front facet 102, diode gain material 103 and lens 104
151 ECDL, external cavity diode laser comprised of AR diode 150, grating 107, PZT 108 and translation stage 109
152 AR modulation source, the subsystem comprised of the AR power supply 115, AR Modulation generator means 116, AR bias T 117, AR power line 110, AR bias T modulation line 111 and AR Laser feed line 112
201 modulation enhanced laser
202 pulser
203 lambda system
204 control unit
211 first photo detector
212 second photo detector
221 first laser beam
222 second laser beam
223a third laser beam
223b fluorescence light
224 first feeder line
225 second feeder line
226 first control line
227 second control line
1000 FSR-matched modulated laser
2000 FSR-matched modulated AR laser
3000 experimental setup
4000 atomic spectrometer Referring now to the drawings, FIG. 4 is a graphical illustration of enhancement of the amplitude of the modulated sidebands due to the matching of the FSR of the laser's resonance cavity to the modulation frequency, in accordance with an embodiment of the present invention. As the FSR is equal to the modulation frequency $f_m$, the frequency spacing of the modulated sidebands matches the frequency spacing of the modes of the resonance cavity of the laser. Thus it is possible that each of the sidebands excite a mode of the laser's resonance cavity, each sideband fulfill the resonance condition of the resonance cavity and thus all the sidebands are amplified by the combined effect of the laser's resonance cavity and the laser's gain material. As seen in FIG. 3, in the prior art such amplification was not possible, as only one sideband, or the un-modulated beam can fulfill the resonance condition at the same time. As a result, in prior art modulation lasers most of the sidebands are suppressed by the laser's resonance cavity, leading to poor modulation efficiency.

Figure 5:
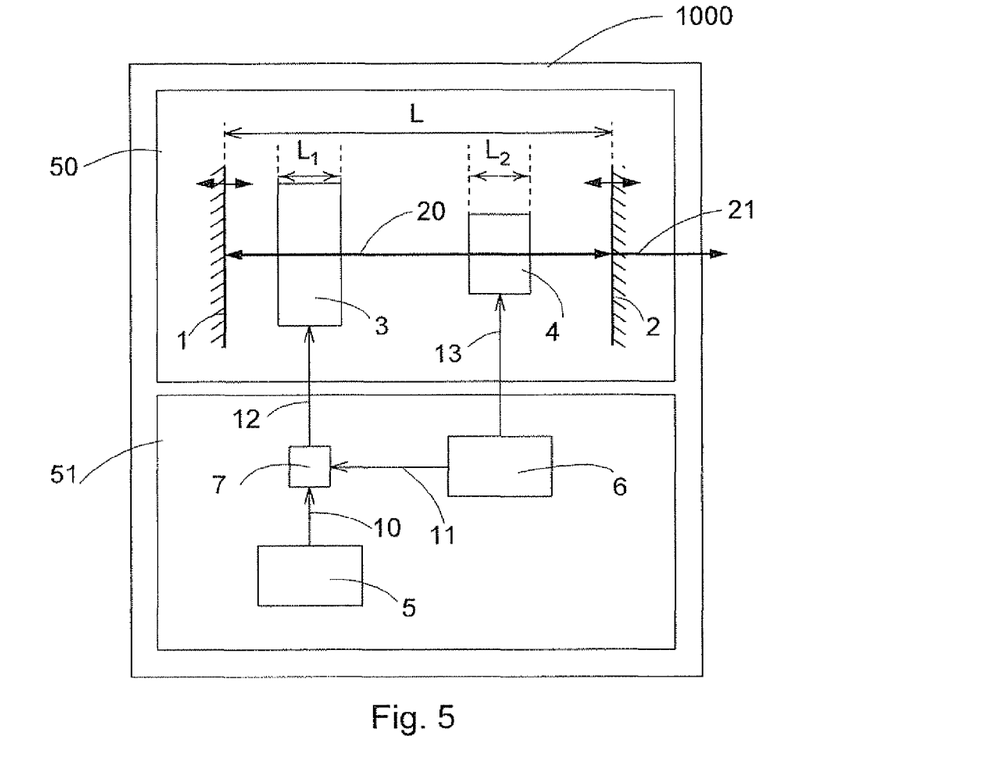
FIG. 5 is a block diagram that schematically illustrates a generic system of FSR-matched modulated laser, in accordance with an embodiment of the present invention.

FIG. 5 is a block diagram that schematically illustrates a generic system of FSR-matched modulated laser 1000, in accordance with an embodiment of the present invention.

The FSR-matched modulated laser 1000, according to the present invention, enhances the efficiency of modulation of laser beams with a periodic signal at frequency $f_m$. The enhancement is achieved by modulating the laser beams inside the resonance cavity of the laser and modifying the free spectral range (FSR) of the resonance cavity so that $FSR=f_m/n$, $n=1, 2, 3 \ldots$.

The enhancement is due to the fact that when laser beam is modulated according to the present invention, both the un-modulated beam and all the modulated sidebands are amplified by the laser's resonance cavity and gain material. Alternatively, the FSR can be modified so that $FSR=2 \times f_m$, and then the un-modulated beam and all even sidebands are amplified by the laser's resonance cavity and gain material.

The FSR-matched modulated laser 1000 is comprised of a laser that can be modulated (M-laser) 50 and a modulation source 51.

M-laser 50 is comprised of back reflector 1 and output coupler 2, with gain medium 3 and optionally light modulation means 4 located between the back reflector 1 and the output coupler 2.

The back reflector 1 and the output coupler 2 create between them a resonance cavity of length L with characteristic free spectral range (FSR) given by (1), shown here again for convenience of reading:

$$FSR = \frac{c}{2L_{eff}}, \quad L_{eff} = L_1 n_1 + L_2 n_2 + (L - L_1 - L_2)n \quad (1)$$

where the FSR is in units of Hz, c is the speed of light given in m/sec, $L_1$ is the width of gain medium 3 in meters, $n_1$ is the refractive index of the gain medium 3, $L_2$ is the width of the light modulation means 4 in meters, $n_2$ is the refractive index of the light modulation means 4 and n is the refractive index of the media that fills the rest of the resonance cavity (typically air or vacuum). The FSR of the resonance cavity is adjustable, optionally by changing length L by moving output coupler 2 towards or away from the back reflector 1 or optionally by changing length L by moving back reflector 1 towards or away from the output coupler 2 or optionally by changing refractive index $n_1$.

As the length L is changed, the FSR is also changed according to Equation (1), so that one can vary the FSR by adjusting the length L and/or refractive index $n_1$.

Modulation source 51 comprised of laser power supply 5, modulation generator 6, bias T 7, power line 10, bias T modulation line 11, laser feed line 12, and direct modulation line 13. Power line 10 feeds power from laser power supply 5 to bias T 7. Optionally, direct modulation line 13 is removed, bias T modulation line 11 feeds the modulation signal from modulation generator 6 to bias T 7, bias T 7 superimposes the power with the modulation signal and laser feed line 12 then feeds the power superimposed with the modulation signal to gain material 3. This option will be referred to as gain material modulation. Alternatively, bias T modulation line 11 is removed, laser feed line 12 then feeds the power from bias T 7 to gain material 3, and direct modulation line 13 feeds the modulation signal to the light modulation means 4. This option will be referred to as direct light modulation.

As known to those familiar with the art to which this invention relates, the lasing condition is that as the internal laser beam 20 passes from the back reflector 1 to the output coupler 2 and back to the back reflector 1, the decrease of the intensity of internal laser beam 20 due to losses is smaller than the increase of the intensity of internal laser beam 20 due to the light amplification of the gain medium 3.

As also known to those familiar with the art to which this invention relates, the frequency of a laser beam such as the internal laser beam 20 (and thus also the frequency of the output laser beam 21) is subject to the following condition known as the resonance condition (2), shown here again, for convenience of reading:

$$v = k \times FSR, k=1,2,3,\ldots \quad (2)$$

where v is the frequency of the internal laser beam 20, in Hz, and k is an integer.

Typically for lasers operating in the infra-red, visible or ultra-violet range, $k \gg 1$.

As also known to those familiar with the art to which this invention relates, in some lasers, when the power fed to the gain medium 3 is superimposed with modulation signal at frequency $f_m$, the internal laser beam 20, and thus also the output laser beam 21, will have additional spectral components, known as sidebands, at frequencies of $v \pm f_m$, $v \pm 2f_m$, $v \pm 3f_m$, .... In this case it is customary to refer to the laser as modulated laser, to refer to the internal laser beam 20, and also to the output laser beam 21 as modulated laser beams, to refer to the un-modulated component of the laser beam (the spectral component with frequency v) as the carrier, to refer to the sidebands as +1 sideband, −1 sideband, +2 sideband, −2 sideband and so on and to refer to the process of generating the sidebands as modulation.

As also known to those familiar with the art to which this invention relates, there are light modulation means 4 such that when fed with modulation signal at frequency $f_m$, a laser beam (such as internal laser beam 20, or output laser beam 21) that passes through light modulation means 4 will be modulated with sidebands at frequencies of $v \pm f_m$, $v \pm 2f_m$, $v \pm 3f_m$, .... In this case it is also customary to refer to the un-modulated component of the laser beam (the spectral component with frequency v) as the carrier and to refer to the sidebands as +1 sideband, −1 sideband, +2 sideband, −2 sideband and so on, to refer to the process of generating the sidebands as modulation and to refer to a laser beam modulated with the sideband as modulated laser beam.

As also known to those familiar with the art to which this invention relates, when the modulation is of a type known as phase modulation, one may define a dimensionless parameter m, called modulation index, which quantifies the intensity of each of the sidebands relative to the intensity of the carrier per the formula:

$$I_{REL \pm k} = \left(\frac{J_k(m)}{J_0(m)}\right)^2, k = 1, 2, 3 \ldots \quad (5)$$

where m is the modulation index, $I_{REL \pm k}$ is the relative intensity of either the +k or the −k sideband and $J_k(m)$ is the $k^{th}$ Bessel function of the first kind.

An exemplary embodiment of the present invention relates to a method and associated system to enable efficient modulation of laser beams.

In the gain modulation option, the gain medium 3 is fed by power from a laser power supply 5 superimposed by the bias T 7 with modulation signal at frequency $f_m$. As a result, the internal laser beam 20 will be modulated with sidebands at frequencies of $v\pm f_m$, $v\pm 2f_m$, $v\pm 3f_m$, ..., and the intensity of each sideband is given by Equation (5).

In the prior art, the FSR of the laser's resonance cavity was not matched to the frequency $f_m$ of the modulation signal. As a result, the sideband's frequencies did not satisfy the resonance condition of the resonance cavity and therefore the intensity of the sidebands was suppressed by the resonance cavity as shown in FIG. 3, resulting small modulation index. According to the present invention the cavity length L of the resonance cavity and/or the refractive index $n_1$ are modified so that the FSR of the resonance cavity is equal to $f_m$ or to $f_m/n$, n=2, 3, 4 ... and then all the sidebands satisfy the resonance condition and all the sidebands are amplified by the resonance cavity and gain material 3. Alternatively, according to the present invention the cavity length L of the resonance cavity and/or the refractive index $n_1$ are modified so that the FSR of the resonance cavity is equal to $2\times f_m$ and then all sidebands of even order (0, 2, ...) satisfy the resonance condition and all the sidebands of even order are amplified by the resonance cavity and gain medium 3.

In the direct light modulation option, the gain medium 3 is fed by power from the laser power supply 5, and modulation signal at frequency $f_m$ is fed to the light modulation means 4. As a result, the internal laser beam 20 will be modulated with sidebands at frequencies of $v\pm f_m$, $v\pm 2f_m$, $v\pm 3f_m$, ..., and the intensity of each sideband is given by Equation (5).

In the prior art, light modulation means such as light modulation means 4 are located outside of the laser's resonance cavity, and thus the sidebands can not be amplified by the resonance cavity. According to the present invention the light modulation means 4 is located inside the resonance cavity and the cavity length L of the resonance cavity and/or the refractive index $n_1$ are modified so that the FSR of the resonance cavity is equal to $f_m$ or to $f_m/n$, n=2, 3, 4, ... and then all the sidebands satisfy the resonance condition and all the sidebands are amplified by the resonance cavity and the gain material 3. Alternatively, according to the present invention the cavity length L of the resonance cavity and/or the refractive index $n_1$ are modified so that the FSR of the resonance cavity is equal to $2\times f_m$ and then all sidebands of even order (0, 2, ...) satisfy the resonance condition and all the sidebands of even order are amplified by the resonance cavity and gain medium 3.

Figure 6:
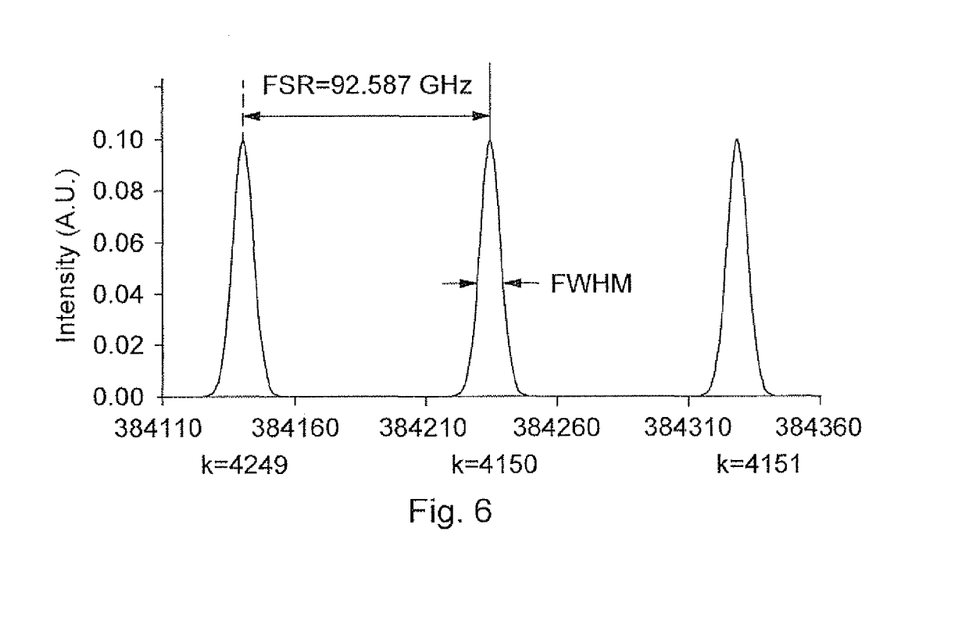
FIG. 6 is a qualitative example of the possible intensity of the light beam inside a resonance cavity as a function of the light's frequency.

FIG. 6 is a qualitative example of the possible intensity of the light beam such as the internal laser beam 20 inside a resonance cavity as a function of the light frequency $v$ in GHz In this example one can note that as the frequency $v$ of a laser beam deviate from the resonance condition the intensity of the light of the laser beam drops sharply. It is customary to call each value of k a mode of the resonance cavity and to say that the laser beam is in the $k^{th}$ mode (or alternatively that the $k^{th}$ mode is excited) if the frequency of the laser beam is equal to $k\times FSR$ for a specific value k. FWHM, the width in Hz at half maximum, is referred to as the width of the modes of the resonance cavity. A laser is called single mode laser if only one of the modes is excited, or multi mode laser if more then one of the modes are excited at the same time.

Figure 7:
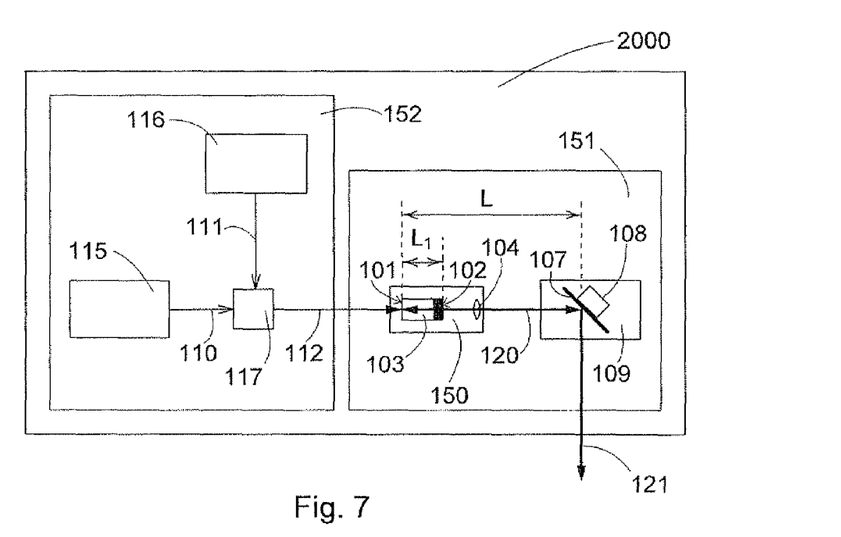
FIG. 7 is a block diagram that schematically illustrates a system of FSR-matched modulated AR laser, in accordance with an embodiment of the present invention.

FIG. 7 is a block diagram that schematically illustrates a system of FSR-matched modulated AR laser 2000, in accordance with an embodiment of the present invention.

As known to those familiar with the art to which this invention relates, the resonance cavity of regular (FP diode) edge emitting laser diode (EELD diode) is between the back facet and the front facet of the FP diode. If the front facet is coated with antireflection (AR) films, then light is no more reflected from the front facet of the EELD back toward the back facet of the EELD, and the lasing condition is not met. An EELD with an AR coated front facet is typically referred to as AR coated laser diode, but the frequency of the light that is transmitted out of AR coated laser diode does not follow resonance condition (2)

As also known to those familiar with the art to which this invention relates, when an AR coated laser diode is placed in an external cavity diode laser configuration similar to ECDL 151, of the present illustration, the grating will function as output coupler, the lasing condition is met and the frequency of the light transmitted out be the grating does follow resonance condition (2) where the free spectral range the of external cavity diode laser ($FSR_{EC}$) is given by $$FSR_{EC} = \frac{c}{2L_{eff}}, \quad L_{eff} = L_1 n_1 + (L - L_1)n \qquad (6)$$

where c is the speed of light in in/sec, L and $L_1$ (in meters) are indicated in FIG. 7, $n_1$ is the refractive index of the gain material of the AR coated laser diode and n is the refractive index of air.

As also known to those familiar with the art to which this invention relates, a configuration similar to the configuration in FIG. 7 was already built and used for modulation of laser light, but only with FP diodes and not with AR diodes.

In the system of FSR-matched modulated AR laser 2000, diode gain material 103 is fed by power from the AR power supply 115 superimposed by the AR bias T 117 with modulation signal at frequency $f_m$. As a result, internal laser beam 120 will be modulated with sidebands at frequencies of $v\pm f_m$, $v\pm 2f_m$, $v\pm 3f_m$, ..., and the intensity of each sideband is given by Equation (5). In the prior art, the $FSR_{EC}$ of the laser's external resonance cavity was not matched to the frequency $f_m$ of the modulation signal. In addition the FSR of the internal resonance cavity of FP diode used in the prior are did not match the frequency $f_m$ of the modulation signal. As a result, the sideband's frequencies did not satisfy the resonance condition of the external resonance cavity and/or the internal resonance cavity of the FP diode and therefore the intensity of the sidebands was suppressed by the external resonance cavity and/or the internal resonance cavity resulting in low modulation efficiency. According to the present invention there is no internal resonance cavity (due to the fact the we use AR diodes) and the cavity length L of the external resonance cavity is modified so that the $FSR_{EC}$ of the external resonance cavity is equal to $f_m$ or to $f_m/n$, n=2, 3, 4, ... and then all the sidebands satisfy the resonance condition and all the sidebands are amplified by the external resonance cavity and the diode gain material 103.

Alternatively, according to the present invention the cavity length L of the external resonance cavity is modified so that the FSR of the resonance cavity is equal to $2\times f_m$ and then all sidebands of even order (0, 2, ...) satisfy the resonance condition and all the sidebands of even order are amplified by the external cavity and the diode gain material 103.

In the present illustration the cavity length L of the external resonance cavity is modified by one of the possible options mentioned in the description of FIG. 5, adjustment of the position of grating 107, which serves here as the output coupler. This description does not in any way exclude the use of any other type of output coupler in the present invention.

Experimental properties, experimental results and conclusions obtained by the present inventors are presented in the following, demonstrating current modulation enhancement of an AR coated edge emitting laser diode placed in an external resonance cavity. By eliminating the internal resonance cavity of the laser diode and matching the FSR of the external resonance cavity to the modulation frequency the modulation response was increased from close to nil up to complete carrier suppression. While not limiting the range of the present invention to a specific power, the maximum power of the modulated laser beam used by the present inventors was measured to be 10 mW.

Experimental Properties

Figure 8:
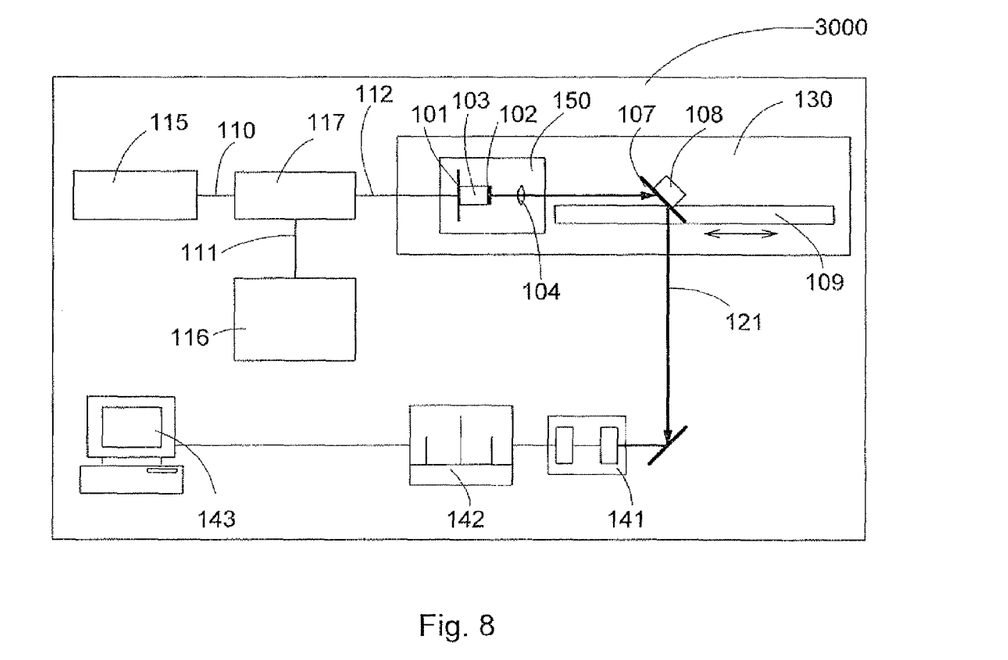
FIG. 8 is a schematic block diagram of an experimental setup of an experiment that was conducted by the present inventors, according to the present invention.

FIG. 8 is a schematic block diagram of an experimental setup 3000 of an experiment that was conducted by the present inventors, according to the present invention. The laser was an external cavity laser diode (ECLD) 130 in the Littrow configuration. The laser AR diode 150 is AR coated (EYP-RWL-0780-00100-1000-SOT01 of Eagleyard).

The diffraction grating 107 is mounted on a piezoelectric transducer (PZT) 108, providing fine tuning and frequency scan. The PZT 108 itself is attached to a 25 mm translation stage 109. Microwave signal generator (maximum power of 20 dBm) is the AR modulation generator 116, providing the microwave modulation signal, which is superimposed onto the diodes DC supply current via a 2.5-6 GHz Bias T 111 (Mini Circuits). The combined signal is then fed to the laser AR diode 150 along a 50 microstrip transmission line, an AR laser feed line 112. The laser wavelength during all measurements was 780 nm corresponding to the $^{87}$Rb D2 line. The frequency modulated (FM) spectrum of the modulated light is detected by scanning Fabry Perot (FP) 141 (FSR of 1 GHz), and is monitored on an oscilloscope 142. The FM spectrum is analyzed by a computer program on a computer 144 to locate the peaks, unfold the "folded" 1 GHz spectrum and calculate the modulation index based on Equation (5), shown here again, for convenience of reading:

$$I_{REL \pm k} = \left(\frac{J_k(m)}{J_0(m)}\right)^2, k = 1, 2, 3 \ldots \quad (5)$$

where m is the modulation index, $I_{REL \pm k}$ is the relative intensity of either the +k or the −k sideband and $J_k(m)$ is the $k^{th}$ Bessel function of the first kind.

Figure 9:
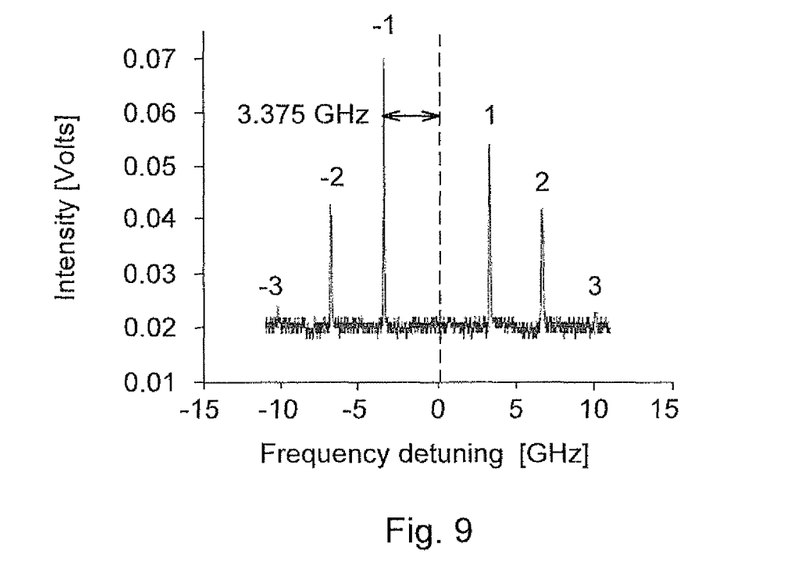
FIG. 9 is a graphical illustration of experimental results obtained from the experiment that was conducted by the present inventors.

An example of the (unfolded) FM modulation picture obtained by the FP is shown in FIG. 9. As noted from FIG. 9 there is sometimes an asymmetry in the intensity of the positive and negative sidebands. This is an evidence of amplitude modulation of the laser's radiation [14]. However, using Equation (5) and substituting $I_{REL \pm k}$ with the average value of the +k and −k sidebands gives a reasonable estimation of the modulation response.

Experiment Results

FIG. 9 is a graphical illustration of experimental results obtained at the experiment that was performed by the present inventors.

A frequency modulation spectrum of the modulated laser diode is shown. The carrier (detuning zero) in this case is completely suppressed.

While modulating the diode laser's current it was noticed that the modulation response increases dramatically at certain modulation frequencies. By scanning the modulation frequency we were able to improve the modulation depth from nil to complete carrier suppression. This is demonstrated in the present drawing.

Figure 10:
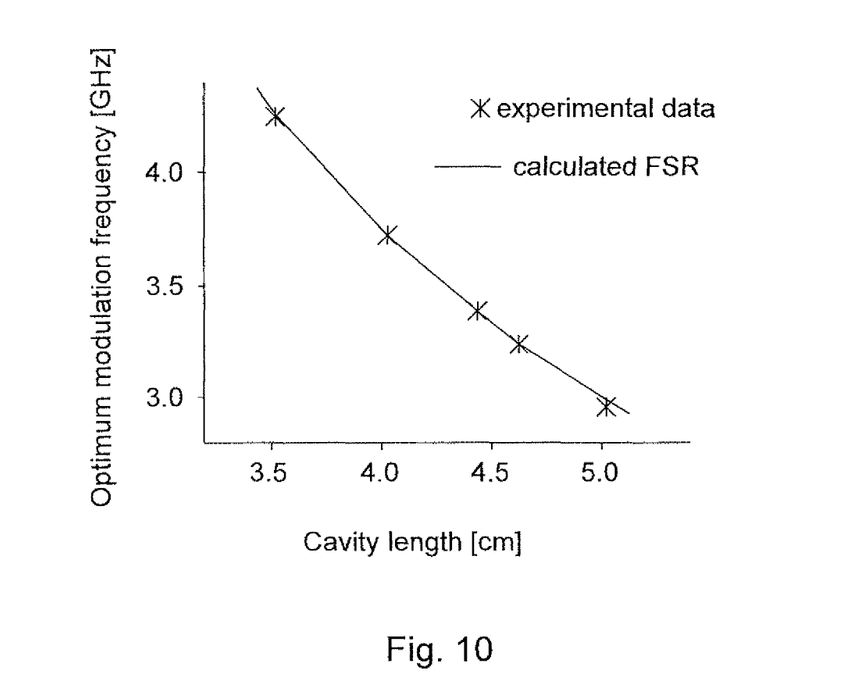
FIG. 10 is another graphical illustration of experimental results obtained from the experiment that was conducted by the present inventors.

FIG. 10 is another graphical illustration of experimental results obtained at the experiment that was performed by the present inventors.

The affect of the resonance cavity length on the modulation response is demonstrated in the present drawing. The experimental data is fitted to the theoretical formula $FSR=c/(2L_{eff})$. The error bars are too small to be shown on this scale. This demonstrates the tunability of this enhanced modulation over a range of more than 3 GHz.

From the graph it is clear that the maximal modulation depth is obtained whenever the modulation frequency corresponds to the FSR resonance condition of the resonance cavity given by equations (2) and (1).

Apparently the optical sidebands are enhanced when they are supported by the modes of the external resonance cavity (the diode itself has no modes since it is AR coated). The width of these modes will determine the width of the modulation response peak (see the inset in FIG. 11). The complete picture is revealed when the modulation frequency is scanned over a wide range. At low frequencies (200-600 MHz) the diode is susceptible to modulation. At this stage both the carrier and the sidebands are supported by the same mode of the external resonance cavity. As the modulation frequency increases, the sidebands decay. The modulation index is suddenly increased again when the modulation frequency is around the value of half the FSR.

Figure 11:
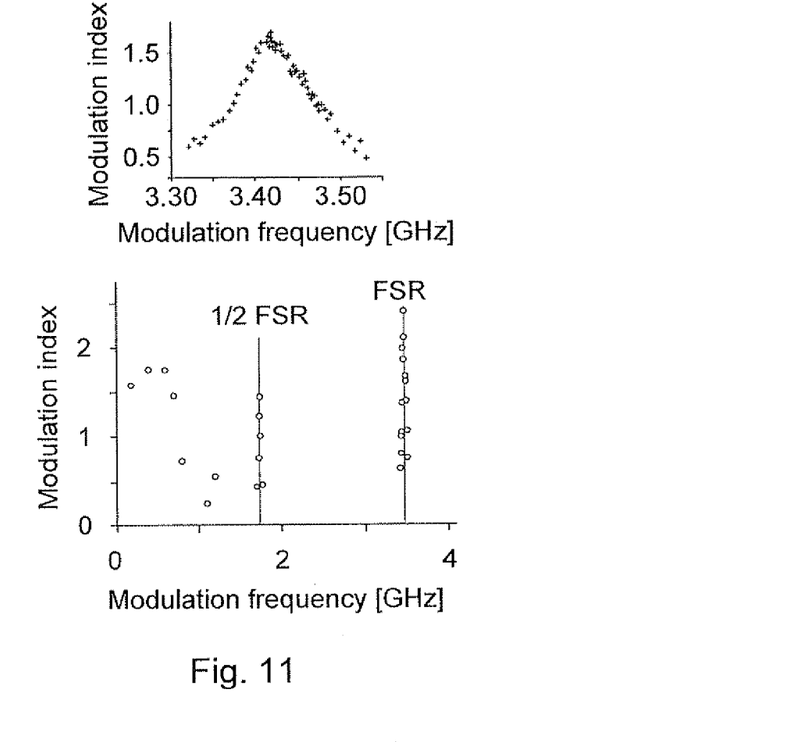
FIG. 11 is a graphical illustration of the modulation response along a wide spectrum of modulation frequencies.

In FIG. 11, a graphical illustration of the modulation response along a wide spectrum of modulation frequencies is presented. The open circles represent experimental data, while the vertical lines denote the modulation frequencies corresponding to half and full FSR of the external resonance cavity. The results of a similar experiment that gives a better resolution of the FSR peak are shown in the inset.

It is important to mention that when the modulation frequency is around the value of half the FSR, only the second optical sidebands were observed. The first sidebands are suppressed since they do not overlap the modes of the resonance cavity. Keeping the scan, the modulation response will decay only in order to be revived again when the modulation frequency matches the FSR. At this point sidebands from both odd and even orders will appear, as they are all supported by the modes of the resonance cavity.

Another important parameter is the DC current. Increasing the injection current will reduce the ratio ($i_m/I_0$) between the modulating current and the DC current leading to a decrease of the modulation index. Such behavior was already reported by [14]. However, in the experiment conducted by the inventors an additional phenomenon relating to the current was observed: the location of the modulation peak in the frequency domain can be controlled by the variation of the current.

Figure 12:
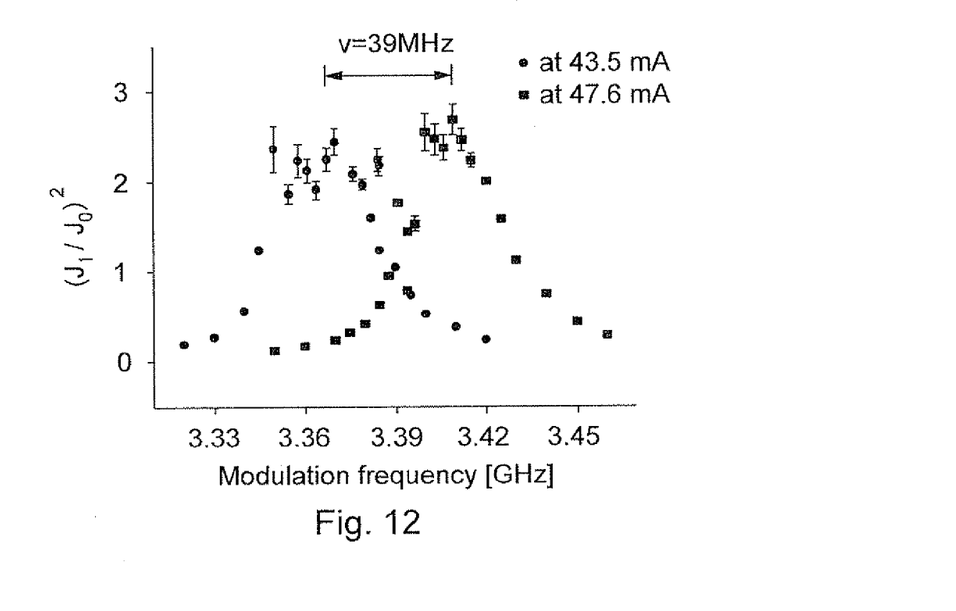
FIG. 12 is a graphical illustration of the modulation response for two current values. The frequency of maximal response is different by 39 MHz.

FIG. 12 is a graphical illustration of the modulation response for two current values. The frequency of maximum modulation response is different by 39 MHz.

A difference of 39 MHz in the modulation peak is achieved by a current shift of 4 mA. While the translation stage enables to match the resonance cavity's FSR to the required modulation frequency in the range of GHz, a fine tuning of the FSR can be done with the PZT, and an auxiliary tuning can be done by the current. A general explanation of this result is that the change of current affects the refraction index of the diode's active medium leading to a change in the effective cavity length.

Figure 13:
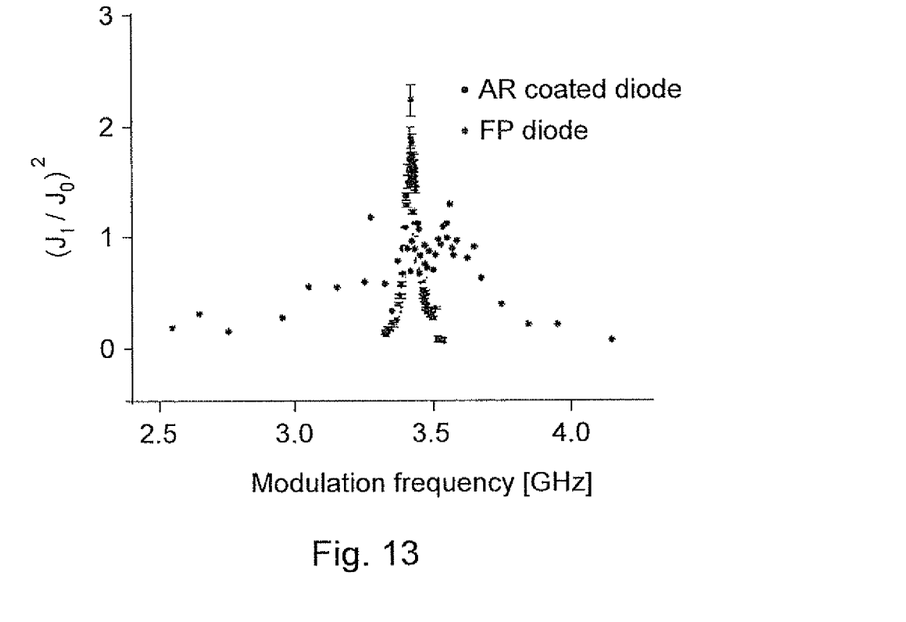
FIG. 13 is a graphical illustration of a comparison between the modulation response of AR coated and FP diodes.

FIG. 13 is a graphical illustration of a comparison between the modulation response of AR coated and FP diodes.

We experimentally tested the modulation response differences between AR (anti reflective) coated and regular FP (Fabry perot) diodes, and the results are summarized in FIG. 13. The measurements were done without changing the cavity length. The results show that although the modulation depth is enhanced around the same frequency, the response peak of the FP diode is much less pronounced. As the distance between the +1 and −1 sidebands, which is twice the modulation frequency, or 6.8 GHz, is of the same order as the width of the FP diode transmission peak, and the FSR is ~150 GHz, the sidebands' intensity is reduced, and full carrier suppression is not possible.

Figure 14:
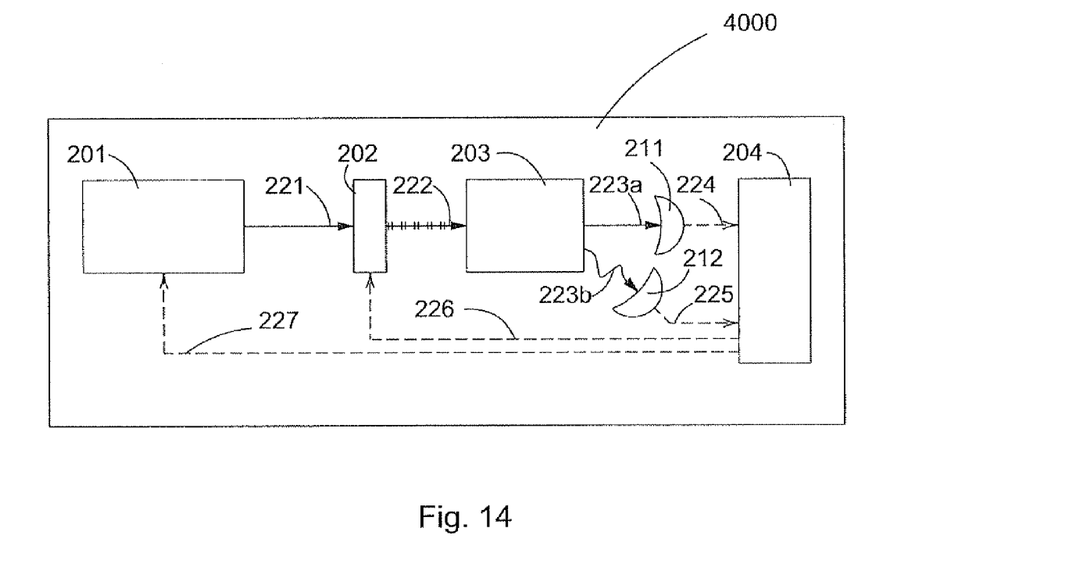
FIG. 14 is a block diagram that schematically illustrates an atomic spectrometer, in accordance with an embodiment of the present invention.

FIG. 14 is a block diagram that schematically illustrates an atomic spectrometer 4000, in accordance with an embodiment of the present invention.

Atomic spectrometer 4000 expresses the advantage of the present invention. The inclusion of a modulation enhanced laser 201 in it, such as a FSR-matched modulated laser (1000) or FSR-matched modulated AR laser (2000), a modulated laser beam containing coherent sidebands with the carrier frequency completely suppressed, enables direct use for quantum interaction with lambda system 203, without the need for filtering of the carrier frequency. Even though this option is also possible when using VCSEL, it is limited to low laser beam intensities (typical total power of the modulated laser beam is below 2 mW), while according to the present invention, there is no need for filtering of the carrier frequency, not even in the case of higher beam intensities.

Atomic spectrometer 4000 includes a modulation enhanced laser 201, such as FSR-matched modulated laser (1000) or FSR-matched modulated AR laser (2000), which generates the first laser beam 221. The first laser beam 221 is a modulated laser beam with carrier frequency $\omega$ and coherent sidebands per Eq. 3 (repeated here):

$$E=E_0 e^{i\omega t}+E_{k\pm}e^{i(\omega\pm k\omega_m)t}, k=1,2,3\ldots \qquad (3)$$

A pulser 202, which receives the first laser beam 221 is a device that can cyclically block and unblock passage through itself of the first laser beam 221, thus enabling the second laser beam 222, which includes pulses generated from the first laser beam 221 to reach lambda system 203. Pulse length can vary between $10^{-7}$ seconds to several minutes.

Figure 15:
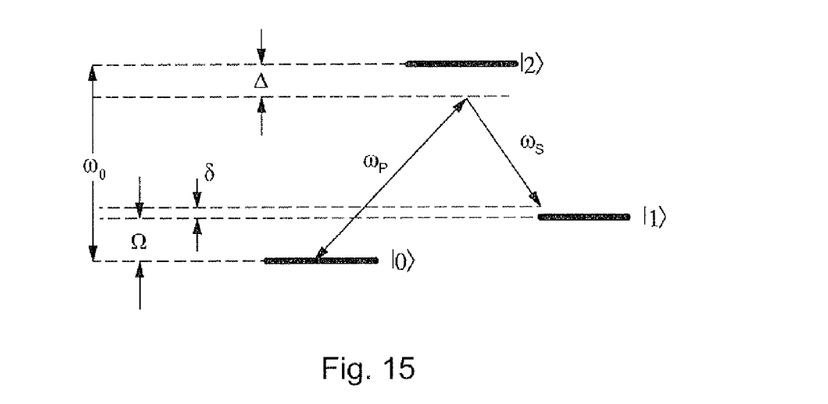
FIG. 15 is a states diagram representing a lambda system, in accordance with an embodiment of the present invention.

Lambda system 203 is a quantum system that is represented by a state diagram as will be shown in FIG. 15, and relates the coherent, modulated sidebands of the second laser beam 222, and constitutes with the coherent sidebands a $\Lambda$ system.

"$\Lambda$ system" is a term known to experts in the field of the invention, and is mentioned in the "Background of the Invention" of the present patent application, and in references provided therein.

Lambda system 203 can transmit two different kinds of light, a third laser beam 223a and a fluorescence light 223b. The third laser beam 223a is the modulated second laser beam 222 after the interaction with lambda system 203. The fluorescence light 223b is the fluorescence produced by the interaction of modulated second laser beam 222 with the lambda system 203.

The atomic spectrometer 4000 also includes two photo detectors, the first photo detector 211, and the second photo detector 212. The first photo detector 211 can measure the intensity of the third laser beam 223a, and the second photo detector 212 can measure the fluorescence light 223b, which is a fluorescence beam.

The atomic spectrometer 4000 also includes a control unit 204. The control unit 204 can vary the frequencies $\omega$ and $\omega_m$ (eq. 3) via second control line 227, can vary the length of a laser pulse via first control line 226, and can interpret the outputs of the first photo detector 211, through the first feeder line 224, and of the second photo detector 212 through the second feeder line 225.

FIG. 14 can, for example, represent an atomic clock were:
(i) the Lambda system 203 is made of mixture of rubidium vapor and other gases in a vacuum tight, transparent container (for rubidium vapor, the value of is very accurately known);
(ii) the control unit 204 includes an adjustable internal oscillator;
(iii) the control 204 unit modifies $\delta$ by modifying $\omega_m$ (Eq. 3) based on signal produced by the adjustable internal oscillator;
(iv) The control unit 204 studies the response of either the first photo detector 211 or the second photo detector 212 to the modifications of $\delta$, and based on that response the control unit 204 corrects the frequency of the adjustable internal oscillator to fit the atomic frequency $\Omega$; and
(v) The corrected frequency of the adjustable internal oscillator (typically 10 MHz) now serve as a basis for clock.

FIG. 15 is a states diagram representing the lambda system 203, in accordance with an embodiment of the present invention.

TABLE 1

| | |
|---|---|
| $\|0\rangle$ | Lower meta-stable quantum state of lambda system 203 |
| $\|1\rangle$ | Upper meta-stable quantum state of lambda system 203 |
| $\|2\rangle$ | Exited quantum state of lambda system 203 |
| $\Omega$ | Energy difference between $\|0\rangle$ and $\|1\rangle$ (measured in units of angular frequency) |
| $\omega_0$ | Energy difference between $\|0\rangle$ and $\|2\rangle$ (measured in units of angular frequency) |
| $\omega_P$ | The angular frequency of the higher frequency sideband |
| $\omega_S$ | The angular frequency of the lower frequency sideband |
| $\Delta$ | Detuning-the difference between $\omega_P$ and $\omega_0$: $\Delta = \omega_0 - \omega_P$ |
| $\delta$ | Small detuning-the difference between $\omega_P$-and $\Omega$: $\delta = \Omega - (\omega_P - \omega_S)$ |

CONCLUSIONS

Enhancement of the modulation response of an AR coated laser diode in an external resonance cavity as a function of the cavity length was demonstrated. The peak modulation frequency is tunable in a range of several GHz. A fine tuning of the modulation depth can be made both with the PZT and by the diode's injection current.

The system enables generation of two coherent laser frequencies without injection locking. The ability to suppress the carrier opens a wide range of applications. For example, injection locking can be used to lock the laser on the higher order sidebands, in order to generate a larger frequency difference (more than 10 GHz). By modulating the diode's current with a frequency corresponding to half the FSR may achieve the same goal, since only the even order sidebands will be enhanced. Another application is offset locking: One of the side bands can be locked to an atomic transition and then inject other sidebands into slaves to amplify them. This method is useful for experiments involving Raman transitions wherein the detuning from the upper level in the $\Lambda$ system has to be much larger then the transition width (the transition width is several MHz while the offset frequency is several GHz).

While the invention has been described with respect to a limited number of embodiments, it will be appreciated that many variations, modifications and other applications of the invention may be made.

What is claimed is:

1. An FSR-matched modulated laser with enhanced modulation efficiency, the FSR-matched modulated laser comprising:
   (a) a M-laser, said M-laser including:
      (i) a back reflector;
      (ii) an output coupler, having a mirror with partial transmission quality, wherein said output coupler is positioned facing said back reflector with a distance L between said output coupler and said back reflector, wherein said distance L is a cavity length;
      (iii) a gain medium disposed between said output coupler and said back reflector; and
      (iv) a light modulation means disposed between said output coupler and said back reflector,
   wherein said M-laser has a free spectral range, wherein said modulation means has a modulation means frequency $f_m$, and wherein said modulation means frequency $f_m$ is equal to an integer times said free spectral range; and
   (b) a modulation source including:
      (i) a laser power supply;
      (ii) a bias T;
      (iii) a power line, said power line feeding power from said laser power supply to said bias T;
      (iv) a modulation generator;
      (v) a bias T modulation line, said bias T modulation line feeding modulation signal from said modulation generator to said bias T;
      (vi) a laser feed line, said laser feed line feeding said power from said bias T to said gain medium; and
      (vii) a direct modulation line, said direct modulation line feeding said modulation signal from said modulation generator to said light modulation means.

2. An FSR-matched modulated laser with enhanced modulation efficiency, the FSR-matched modulated laser comprising:
   (a) a M-laser, said M-laser including:
      (i) a back reflector;
      (ii) an output coupler, having a mirror with partial transmission quality, wherein said output coupler is positioned facing said back reflector with a distance L between said output coupler and said back reflector, wherein said distance L is a cavity length;
      (iii) a gain medium disposed between said output coupler and said back reflector; and
      (iv) a light modulation means disposed between said output coupler and said back reflector,
   wherein said M-laser has a free spectral range, wherein said modulation means has a modulation means frequency $f_m$, and wherein said modulation means frequency $f_m$ is equal to one half of said free spectral range; and
   (b) a modulation source including:
      (i) a laser power supply;
      (ii) a bias T;
      (iii) a power line, said power line feeding power from said laser power supply to said bias T;
      (iv) a modulation generator;
      (v) a bias T modulation line, said bias T modulation line feeding modulation signal from said modulation generator to said bias T;
      (vi) a laser feed line, said laser feed line feeding said power from said bias T to said gain medium; and
      (vii) a direct modulation line, said direct modulation line feeding said modulation signal from said modulation generator to said light modulation means.

3. An FSR-matched modulated AR laser with enhanced modulation efficiency, the FSR-matched modulated AR laser comprising:
   (a) an external cavity diode laser including:
      (i) an AR diode, having a front facet, a back facet, a diode gain material, and a lens, wherein said front facet is coated with anti reflection films;
      (ii) a grating, positioned such that part of an internal AR laser beam that hits said grating is reflected back and another part of said internal AR laser beam is reflected to an output direction as an output AR laser beam; and
      (iii) a mechanical means for controlling a cavity length of said FSR-matched modulated AR laser, by moving said grating for controlling a FSR and a laser frequency of said FSR-matched modulated AR laser with enhanced modulation efficiency,
   wherein said FSR-matched modulated AR laser has a free spectral range, wherein said FSR-matched modulated AR laser is modulated by a modulation means having a modulation means frequency $f_m$, and wherein said modulation means frequency $f_m$ is equal to an integer times said free spectral range, wherein said mechanical means includes:
      a piezoelectric transducer, said piezoelectric transducer is firmly connected to said grating; and
      a mechanical translation stage, wherein said piezoelectric transducer is firmly connected to said translation stage, wherein said piezoelectric transducer can move in a motion direction which is aligned parallel to a direction of said internal AR laser beam; and
   (b) an AR modulation source including:
      (i) an AR power supply, for supplying power to said gain medium;
      (ii) an AR modulation generator, that produces a modulation signal, which is a periodic electrical signal at frequency $f_m$;
      (iii) an AR Bias T, for superimposing said power with said modulation signal;
      (iv) an AR power line, said AR power line feeding said power from said AR laser power supply to said AR Bias;
      (v) an AR bias T modulation line, said AR bias T modulation line feed said modulation signal from said AR modulation generator to the bias T; and
      (vi) an AR laser feed line, said AR laser feed line feeding said power superimposed with said modulation signal from said bias T to said gain medium, wherein said supplying of said power to said gain medium is done through said AR bias T.

4. An FSR-matched modulated AR laser with enhanced modulation efficiency, the FSR-matched modulated AR laser comprising:
   (a) an external cavity diode laser including:
      (i) an AR diode, having a front facet, a back facet, a diode gain material, and a lens, wherein said front facet is coated with anti reflection films;
      (ii) a grating, positioned such that part of an internal AR laser beam that hits said grating is reflected back and another part of said internal AR laser beam is reflected to an output direction as an output AR laser beam; and
      (iii) a mechanical means for controlling a cavity length of said FSR-matched modulated AR laser, by moving said grating for controlling a FSR and a laser frequency of said FSR-matched modulated AR laser with enhanced modulation efficiency, wherein said FSR-matched modulated AR laser has a free spectral range, wherein said FSR-matched modulated AR laser is modulated by a modulation means having a modulation means frequency $f_m$, and wherein said modulation means frequency $f_m$ is equal to one half of said free spectral range, wherein said mechanical means includes:

a piezoelectric transducer, said piezoelectric transducer is firmly connected to said grating; and a mechanical translation stage, wherein said piezoelectric transducer is firmly connected to said translation stage, wherein said piezoelectric transducer can move in a motion direction which is aligned parallel to a direction of said internal AR laser beam; and (b) an AR modulation source including:
  (i) an AR power supply, for supplying power to said gain medium;
  (ii) an AR modulation generator, that produces a modulation signal, which is a periodic electrical signal at frequency $f_m$;
  (iii) an AR Bias T, for superimposing said power with said modulation signal;
  (iv) an AR power line, said AR power line feeding said power from said AR laser power supply to said AR Bias;
  (v) an AR bias T modulation line, said AR bias T modulation line feed said modulation signal from said AR modulation generator to the bias T; and
  (vi) an AR laser feed line, said AR laser feed line feeding said power superimposed with said modulation signal from said bias T to said gain medium, wherein said supplying of said power to said gain medium is done through said AR bias T.

* * * * *